United States Patent [19]

Austin et al.

[11] Patent Number: 5,451,564

[45] Date of Patent: Sep. 19, 1995

[54] ANTIMICROBIAL COMPOSITION COMPRISING N-HYDROXY HETEROCYCLIC THIONES

[75] Inventors: Peter W. Austin; Fraser F. Morpeth, both of Lancs, England

[73] Assignee: Zeneca Limited, London, England

[21] Appl. No.: 219,876

[22] Filed: Mar. 29, 1994

Related U.S. Application Data

[63] Continuation of Ser. No. 839,414, Feb. 21, 1992, abandoned.

[30] Foreign Application Priority Data

Feb. 21, 1991 [GB] United Kingdom ............ 9103631

[51] Int. Cl.$^6$ .................. A01N 43/36; A01N 43/40; A01N 43/78; A01N 43/86
[52] U.S. Cl. ...................... 504/221; 504/248; 504/254; 504/266; 504/283; 514/227.2; 514/328; 514/348; 514/369; 514/425; 514/769; 424/70.1; 71/DIG. 1
[58] Field of Search .......... 504/266, 221, 248, 254, 504/283; 514/369, 769, 227.2, 328, 348, 425; 71/DIG. 1; 424/70.1

[56] References Cited

U.S. PATENT DOCUMENTS

| | | | |
|---|---|---|---|
| 2,686,786 | 8/1954 | Shaw et al. | 260/294.8 |
| 2,758,116 | 8/1956 | Wiselogle et al. | 260/294.8 |
| 4,008,065 | 2/1977 | Hanschild | 71/34 |
| 4,323,466 | 4/1982 | Curry et al. | 514/401 |
| 4,933,011 | 6/1990 | Rei | 106/18.31 |
| 5,250,500 | 10/1993 | Jones et al. | 504/165 |

FOREIGN PATENT DOCUMENTS 0249328 12/1987 European Pat. Off.
0257533 3/1988 European Pat. Off.

OTHER PUBLICATIONS

Chemical Patents Index, Basic Abstracts Journal, Sec. Ch, Week 8316, JP 58041802, Derwent Publications Ltd., London, GB Mar. 1983.
Chemical Patents Index, Basic Abstracts Journal, Sec. Ch, Week 8311, SU 926249, Derwent Publications Ltd., London, GB May 1982.

*Primary Examiner*—S. Mark Clardy
*Attorney, Agent, or Firm*—Cushman Darby & Cushman

[57] ABSTRACT

A composition comprising (a) a metal salt or complex with an organic compound of the general formula

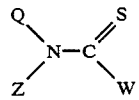

and (b) an oxy-phosphorus compound where W may be —SH or an optionally substituted hydrocarbyl group, Q is —OH, hydrogen or optionally substituted hydrocarbyl and Z is hydrogen or optionally substituted hydrocarbyl and Q and Z or Z and W may complete a ring. The compounds are typically metal complexes of thiohydroxamic acids or dithiocarbamates. The metal is typically zinc.

The compositions exhibit improved aqueous solubility compared with the metal complexes alone, and can be used as industrial biocides, especially fungicides and particularly in paint films and latices.

11 Claims, No Drawings

ANTIMICROBIAL COMPOSITION COMPRISING N-HYDROXY HETEROCYCLIC THIONES

This is a continuation of Application No. 07/839,414, filed on Feb. 21, 1992, which was abandoned upon the filing hereof.

The present invention relates to a composition comprising the metal salts or complexes of thiohydroxamic acids or of dithiocarbamates with an oxy-phosphorus containing compound and the use of such compositions as industrial biocides.

Industrial biocides are useful to prevent industrial spoilage, in particular that caused by bacteria and fungi. Materials which can be used as industrial biocides have antimicrobial properties and particularly have antifungal or antibacterial properties or preferably both antifungal and antibacterial properties. Such materials are useful in the preservation of paints, latices, adhesives, leather, wood, metal working fluids and cooling water.

In our European Patent Application Publication No 0249328 we disclose certain cyclic thiohydroxamic acid derivatives and the metal salts or complexes thereof and the use of such compounds as anti-microbial agents. These compounds include 3-hydroxy-4-methylthiazol-2(3H)-thione and derivatives thereof including metal complexes and salts such as the zinc complex of 3-hydroxy-4-methylthiazol-2(3H)-thione.

Certain cyclic thiohydroxamic metal complexes have become established as important industrial biocides, especially the metal complexes of 1-hydroxy-2-pyridinethiones as disclosed for example in U.S. Pat. Nos. 2,686,786, 2,758,116 and 2,809,971.

Metal complexes of acyclic thiohydroxamic acids are also disclosed in Acta. Chem. Scand.1967 (21), page 1936 and Australian Journal of Chemistry 1977 (30) page 2439. In J.Antibiot 1970 (23) 546 and 1971 (24) 124, the iron and copper complexes of N-methyl-N-hydroxythioamide are disclosed as naturally occurring antibiotics.

Many metal salts and complexes of the thiohydroxamic acids and dithiocarbamates exhibit low solubility, especially in water or aqueous systems. Consequently, many require formulating as either aqueous dispersions or emulsions. The production of aqueous dispersions in particular is both costly and time consuming and often gives rise to technical difficulties in preparing compounds with optimal particle size.

Even when such dispersions have been formed, they often exhibit stability deficiencies under storage conditions. Thus separation, sedimentation and/or aggregation of the microbial agent from the formulation can occur and this gives rise to problems in uniform metering of the correct dosage of the microbial agent during industrial usage. Separation of the microbial agent when used in certain applications such as to preserve latices and paints can also occur leading to loss or impairment of microbiological control.

A further consequence of the low aqueous solubility of the metal complexes of the thiohydroxamic acids and dithiocarbamates is that the microbiological activity is often very dependent on the particle size of the active ingredient, and in many instances the microbiological activity of the compound is lower than would be the case if the compound had higher aqueous solubility.

Thus, it is desirable to provide a metal salt or complex of the foregoing type which has an improved aqueous solubility.

We have now found that the aqueous solubility of certain metal complexes which are useful as industrial biocides may be improved in the presence of an oxy-phosphorus compound.

According to the present invention there is, thus, provided a composition comprising (a) a metal salt or complex with an organic compound of general formula I

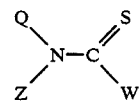

wherein

Z is hydrogen or hydrocarbyl which may be substituted and wherein the hydrocarbyl group contains up to 10 carbon atoms;

Q is hydrogen, —OH, hydrocarbyl which may be substituted and wherein the hydrocarbyl group contains up to 10 carbon atoms, or Q and Z together with the nitrogen atom to which they are attached form a heterocyclic ring;

W is —SH, hydrocarbyl which may be substituted and wherein the hydrocarbyl group contains up to 10 carbon atoms, or W and Z together with the nitrogen and carbon atoms to which they are attached form a heterocyclic ring; provided that Z and Q are not both hydrogen; and either Q is —OH, or W is —SH and when W is —SH, Q is not —OH and when Q is —OH, W is not —SH; and (b) an oxy-phosphorus compound.

In the organic compound of general formula I, when any one or more of Z, Q or W is substituted hydrocarbyl the substituent group contains at least one hetero atom selected from nitrogen, oxygen, sulphur or a halogen atom such as fluorine, chlorine or bromine.

It should be understood that certain organic compounds of formula I may exist in a different tautomeric form. This is most readily appreciated in the organic compounds of general formula I where Q is —OH and Z and W complete a dihydropyridine ring as in 1-hydroxy-2(1H)pyridinethione which, as is disclosed in U.S. Pat. Nos. 2,686,786 and 2,089,971, may be in tautomeric equilibrium with the corresponding 2-mercaptopyridine-1-oxide.

In one embodiment of the present invention, the metal salt or complex with an organic compound is a metal salt or complex of an organic compound of general formula II

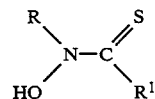

wherein R and R¹, which may be the same or different, are hydrocarbyl groups or substituted hydrocarbyl groups wherein the hydrocarbyl group contains up to 10 carbon atoms, or where R and R¹, together with the nitrogen and carbon atoms to which they are attached, form a heterocyclic ring.

Typically, the groups R and R¹ may be alkyl, cycloalkyl, aryl, aralkyl, or alkaryl groups and contain from 1 up to 10 carbon atoms. If one, or both, of the groups R and R¹ is substituted, the substituent or each substituent may be a hydrocarbonoxy group; an acyl group; an ester (that is an acyloxy) group, a halogen atom or a nitrile group. Alternatively, the substituent may be a heteroatom in a heterocyclic group, which may itself be substituted with substituents as hereinbefore described. Heterocyclic groups include pyridyl, thienyl, imidazoyl, and thiazoyl. If R and/or $R^1$ is an alkyl group, it is preferably a lower alkyl group, that is one containing not more than five carbon atoms. If R and/or $R^1$ is a cyclic, including heterocyclic, group, it preferably contains at least five, and particularly at least six, atoms. The groups R and $R^1$ may be the same but preferably are different. R is especially a lower alkyl group such as a methyl group and it is preferred that R is not an aralkyl group, especially one in which there is only one carbon atom between the aryl group and the nitrogen atom. $R^1$ can be an alkyl group, especially a lower alkyl group such as methyl, ethyl, n-propyl or i-propyl or can be a cyclic group such as a phenyl group.

Where the groups R and $R^1$ together with the nitrogen and carbon atoms to which they are attached form a heterocyclic ring, the metal salt or complex is typically a metal salt or complex with an organic compound of general formula III

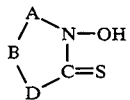

III wherein:

A is a nitrogen or carbon atom, which may be substituted; or a group —CH—CH—;

B and D are, independently, oxygen or sulphur or a nitrogen or carbon atom which may be substituted; or A and/or B and/or B and/or D may be part of a ring system; with the proviso that B and D are not both sulphur or both oxygen.

The group A, and optionally one or both of groups B and D can be a

—$C(R^2)_2$; a group —$CR^2$=; a group

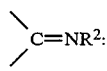

a group —$NR^2$— or a group —N=; where $R^2$ is a hydrogen atom, a hydrocarbyl group, a substituted hydrocarbyl group or two groups $R^2$ together with the carbon atom or carbon atoms to which they are attached form a ring.

When $R^2$ is hydrocarbyl, it is preferably $C_{1-5}$ lower alkyl, phenyl or substituted phenyl.

The groups A, B and D can form part of a further ring system but generally not more than two of the groups A, B and D form part of a further ring system. The further ring system is preferably a hydrocarbon ring system containing five or six carbon atoms, for example a cyclopentene, cyclohexane, cyclohexene, cyclohexadiene or benzene ring. The further ring system, if present, preferably contains one or both of the groups A and B. If only the group A forms part of a ring system, this may be a cyclohexane ring of the type

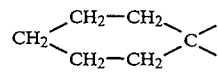

where the group A is the carbon atom with the two free valencies, which are linked to the group —NOH— and B respectively. If both A and B form part of a ring system, the further ring is then fused to the azolethione ring system; for example as in 3-hydroxy-4,5,6,7-tetrahydrobenzothiazol-2(3H)-thione.

In many of the compounds used in the biocide compositions of the present invention, the groups A, B and/or D are not part of a further ring system. Thus, if A, B and/or D is a carbon atom, or substituted carbon atom, it may be, inter alia, a group —CH=, —$C(CH_3)$=, —$C(C_2H_5)$=, —$C(C_6H_5)$=, —$C(C_6H_4Cl)$=, —$C(CH_3)_2$ or

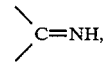

or, for A only, a group —CH=CH—. It will be appreciated that in the foregoing, the group $R^2$ is a hydrogen atom, a methyl, ethyl, phenyl or chlorophenyl group.

In one preferred embodiment, the groups A and B are both optionally substituted carbon atoms and the group D is a sulphur atom or optionally substituted nitrogen atom. The groups A and B are preferably linked through a double bond to form a group such as the group —CH=CH—. It is preferred that D is a sulphur atom.

In yet another preferred embodiment where A is the group —CH=CH— and B and D are both substituted carbon atoms, A, B and D together with the nitrogen and carbon atoms in the compound of general formula III may complete a dihydro pyridine ring. The compound of general formula III is thus 1-hydroxy-2(1H)-pyridinethione.

In yet another embodiment of the present invention, the metal salt or complex with an organic compound is a metal salt or complex of an organic compound of general formula IV

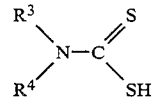

IV wherein $R^3$ and $R^4$, which may be the same or different, are hydrogen, hydrocarbyl which may be substituted wherein the hydrocarbyl group contains up to 10 carbon atoms, or where $R^3$ and $R^4$ together with the nitrogen atom to which they are attached form a heterocyclic ring; provided that $R^3$ and $R^4$ are not both hydrogen.

When one or both of $R^3$ and $R^4$ is hydrocarbyl, it is preferably an alkyl, cycloalkyl, aryl or alkaryl group and contains from 1 up to 10 carbon atoms.

When one or both of $R^3$ and $R^4$ is substituted hydrocarbyl, it is hydrocarbyl containing at least one heteroatom selected from the group oxygen, nitrogen, sulphur or a halogen atom such as fluorine, chlorine and bromine.

When $R^3$ and $R^4$ together with the nitrogen atom to which they are attached form a ring, the ring may additionally contain other heteroatoms selected from sulphur, oxygen and nitrogen itself. Typical examples of such rings are morpholine, piperidine and piperazine rings.

It is preferred, however, that at least one of $R^3$ and $R^4$ is alkyl, which may be linear or branched, and which contains up to 10 carbon atoms, and especially which contains up to 4 carbon atoms such as methyl.

In one specific embodiment where $R^3$ is a substituted hydrocarbyl group, the hydrocarbyl group is an alkylene moiety which is itself substituted by a dithiocarbamate group.

In yet another specific embodiment where $R^3$ and $R^4$ together with the nitrogen to which they are attached form a piperazine ring, both nitrogen atoms may be further substituted to form a dithiocarbamate group.

The metal salt or complex with an organic compound which is component (a) of the composition of the present invention is a metal salt or complex of a metal of Groups IIIA to VA or IB to VIIB of the Periodic Table. All references herein to the Periodic Table are to the Periodic Table according to Mandeleeff, as set out on the inside rear cover of "Handbook of Chemistry and Physics" 49th Edition (1968–1969) published by The Chemical Rubber Co., Cleveland, Ohio, USA.

As will be readily appreciated, one or more metals may be used simultaneously when forming the metal salt or complex of the organic compound of general formula I such that the metal salt or complex contains two or more different metals. In such cases, the metal salt or complex is a mixture of the metal salts or complexes derived from an organic compound of the general formula I.

It is generally preferred, however, to react one metal with an organic compound of the general formula I.

We have obtained compounds having useful properties when the metal is a metal of Group IIB of the Periodic Table, for example zinc.

It will be appreciated that when preparing metal salts or complexes with organic compounds of general formula I, the metal salt or complex of the organic compound may contain ligands which give a neutral molecule, and the nature of these ligands depends upon the particular method and conditions of preparation. Thus, the metal salt or complex of the organic compound of general formula I may contain ligands which include, for example, water, halides such as chloride, alcohols, ketones, carboxylic acids, amines, sulphoxides and the like. The ligand, if present, typically results from the reagents or solvents used to prepare the metal salt or complex of the organic compound and, in particular, the ligand results from the solvent used during the preparation of the metal salt or complex. The ligand may be a mixture of anionic groups and neutral ligands. In general, the ligand when present, is water.

The ratio of the organic compound of general formula I to the metal in the metal salt or complex can vary depending on the actual metal used and also depending on the valency of the metal. The ratio may also vary depending on the number of sites in the organic compound which are capable of forming a salt or complex with the metal. Typically, where there are two sites in the organic compound capable of forming a salt or complex with a metal as in the thiohydroxamic acids and dithiocarbamates and the metal is divalent, for example, Cu(II), Zn(II) or Fe(II) the metal salt or complex will contain 2 parts organic compound to 1 part metal i.e. a 2:1 complex. When the metal is Fe(III), the metal salt or complex formed is typically a 3:1 complex of organic component to metal.

When the organic compound contains more than two sites capable of forming a metal salt or complex as in the case for example of ethylenebis dithiocarbamate which contains four sites, the metal salt or complex formed is more complex. The metal salt or complex of ethylenebisdithiocarbamate with divalent metals such as Cu(II) or Zn(II) typically analyses as a 1:1 complex.

As specific examples of the metal salt or complex of the acyclic thiohydroxamic acid which is component (a) there may be mentioned the 2:1 complex obtained from N-methyl-N-hydroxythiobenzamide (formula II where R is methyl and $R^1$ is phenyl) and zinc, the 2:1 complexes obtained from N-methyl-N-hydroxythioacetamide; N-methyl-N-hydroxythiopropionamide; N-methyl-N-hydroxythioisobutyramide, or N-methyl-N-hydroxythiobutyramide and zinc, which are the zinc complexes of a compound of general formula II where R is methyl, and $R^1$ is methyl, ethyl, isopropyl or n-propyl respectively.

As specific examples of the metal salts or complexes of the cyclic thiohydroxamic acids there may be mentioned the 2:1 complex obtained from 3-hydroxy-4-methylthiazol-2(3H)-thione (formula III where A is the group —(CH$_3$)C=, B is —CH=, and D is sulphur) and zinc, the 3:1 complex obtained from 3-hydroxy-4-methylthiazol-2(3H)-thione (formula III where A is the group —(CH$_3$)C=, B is —CH= and D is sulphur) and Fe(III), the cupric complex of 1-hydroxy-4-imino-3-phenyl-2-thion-1,3-diazaspiro[4,5]decane (formula III where A is cyclohexyl, B is —NH— and D is —N(C$_6$H$_5$)—), the cupric complex of 4,5-dimethyl-3-hydroxythiazol-2(3H)thione (formula III where A is the group —(CH$_3$)C=, B is the group —(CH$_3$)C= and D is sulphur), the zinc complex obtained from 4,5-dimethyl-3-hydroxythiazol-2(3H)thione (formula III where A is the group —(CH$_3$)C=, B is the group —(CH$_3$)C= and D is sulphur), the zinc complex of 4-ethyl-3-hydroxy-5-methylthiazol-2(3H)thione (formula III where A is the group —(C$_2$H$_5$)C=, B is the group —(CH$_3$)C= and D is sulphur) and the zinc complex obtained from 1-hydroxy-2-pyridinethione (formula III where A is the group —CH=CH—, B is —CH= and D is —CH=).

As specific examples of the metal salts or complexes of the dithiocarbamate of general formula IV there may be mentioned the 2:1 zinc complex of dimethyldithiocarbamate (formula IV, $R^3$ and $R^4$ are both methyl) and the zinc complex of ethylene bisdithiocarbamate. This latter compound is normally regarded as a 1:1 zinc complex (ie the actual salt or complex with the compound of formula IV, $R^3$ is ethylene dithiocarbamate (—CH$_2$CH$_2$NHC(S)S—) and $R^4$ is hydrogen).

Such compounds may also contain more than one metal, such that the dithiocarbamate of general formula IV is a mixture of metal complexes.

Many metal complexes of the dithiocarbamates of general formula IV are often referred to by their trivial names such as ZIBAM, ZIRAM, ZINEB and MANEB.

The metal salts or complexes which are component (a) in the composition of the present invention can be prepared using known techniques for the preparation of metal salts or complexes. Conveniently the metal salt or complex is prepared by the reaction of a salt of the metal with an N-hydroxythioamide. More specifically, a salt of the metal is reacted with an N-hydroxythioamide of the formula II.

The salt of the metal is preferably used as a solution in a suitable solvent. Thus, the salt may be an acetate such as zinc acetate which is dissolved in water or an alcohol, for example methanol.

The acyclic N-hydroxythioamide may be N-methyl-N-hydroxythiobenzamide, N-methyl-N-hydroxythioacetamide, N-methyl-N-hydroxythiopropionamide, N-methyl-N-hydroxythtotsobutyramide or N-methyl-N-hydroxythiobutyramide. A less preferred N-hydroxythioamide is N-benzyl-N-hydroxythioacetamide. N-hydroxythioamides may be prepared using known procedures, for example as described in Acta Chemica Scand 1967 (21) 1936.

The cyclic-N-hydroxythioamide may be 3-hydroxy-4-methylthiazol-2(3H)-thione,
3-hydroxy-phenylthiazol-2(3H)-thione,
3-hydroxy-4,5,6,7-tetrahydrobenzothiazol-2(3H)-thione,
5,5-dimethyl-1-hydroxy-4-imino-3-phenylimidazolidine-2-thione,
1-hydroxy-4-imino-3-phenyl-2-thion-1,3-diazaspiro[4,5]decane,
4,5-dimethyl-3-hydroxythiazol-2(3H)-thione,
4-ethyl-3-hydroxy-5-methylthiazol-2(3H)-thione,
4-(4-chlorophenyl)-3-hydroxythiazol-2(3H)-thione,
3-hydroxy-5-methyl-4-phenylthiazol-2(3H)-thione,
1-hydroxy-2-pyrrolidinthione,
5,5-dimethyl-1-hydroxy-2-pyrrolidinthione,
2-hydroxy-2,3-dihydro-1H-isoindol-1-thione or
1-hydroxy-2-pyridinethione.

The dithiocarbamate may be a salt of dimethyldithiocarbamic acid or ethylene bisdithiocarbamic acid, for example their sodium or ammonium salts.

The reaction is conveniently effected by mixing together solutions, in the same solvent, of the salt of the metal and the compound of general formula I. The solutions can be mixed together without heating the mixture. However, whilst the reaction can be effected at essentially ambient temperature (15°–20° C.), higher or lower temperatures may be used, for example from 0° C. up 100° C., although it is generally not preferred to use a temperature in excess of 50° C.

The reaction is preferably effected in a liquid which is a solvent for the reactants but a non-solvent for the metal salt or complex obtained. Thus, the reaction may be carried out in aqueous alkaline solution by dissolving the organic compound of formula I in water and adding sufficient alkali, such as sodium hydroxide, to dissolve the organic compound, and then mixing with an aqueous solution containing the metal salt. Alternatively, the reaction may be carried out in a solvent such as ethanol in which both components of the reaction are soluble. The reaction may also be carried out by dissolving one of the components in water, and adding the other component as a solution in a water-miscible solvent. The metal salt or complex is typically a solid and is formed as a precipitate during the reaction. The solid is readily separated from the reaction mixture, for example by filtration. The solid is then washed to remove impurities, for example using water, the solvent used for the preparation or both in sequence and/or as a mixture.

The reaction is conveniently effected by mixing together solutions of the two reactants and stirring to effect reaction. If the metal complex separates as a solid, stirring of the reaction mixture is continued from 0.1 up to 10 hours, for example 0.5 up to 2 hours. Stirring is then terminated and the solid is separated, conveniently by filtration but other techniques such as allowing the solid to settle and removing the supernatant liquid phase may also be used.

The metal salt and the organic compound of general formula I are conveniently reacted together in the stoichiometric quantities required to obtain the desired metal salt or complex.

The oxy-phosphorus compound which is component (b) of the composition may be any acid or salt of an acid which contains both phosphorus and oxygen atoms. It thus includes the simple anions formed between phosphorus and oxygen such as ortho phosphoric acid and its salts, orthophosphites, hypophosphites and the polymeric oxy-phosphorus anions such as triphosphates or tripolyphosphates, hexametaphosphates and especially pyrophosphates.

The oxy-phosphorus compound may be in the form of its free acid or it may be in the form of a salt formed with an alkali metal, ammonia or an amine.

It will be appreciated that the oxy-phosphorus compound may contain different cations, especially mixtures of hydrogen, ammonia and alkali metal cations.

As a specific examples there may be mentioned trisodium orthophosphate, disodium hydrogen orthophosphate, tetrasodium pyrophosphate, disodiumdihydrogen pyrophosphate, tetrapotassium pyrophosphate, tetralithium pyrophosphate, tetraammonium pyrophosphate and disodium bisdiethanolamine pyrophosphate.

In many instances, we have found that a complex is formed between the metal salt or complex and the pyrophosphate which contains equimolar amounts of the metal complex which is component (a) and the pyrophosphate which is component (b). However, it is generally more convenient to prepare compositions according to the invention where the pyrophosphate is present in greater molar amounts relative to the salt or metal complex.

Thus, the ratio of the metal salt or complex which is component (a) of the composition of the present invention to the oxy-phosphorus compound which is component (b) can vary between 1:1 and 1:10,000 parts by weight, and especially between 1:1 and 1:1000 parts by weight.

We have found that particularly useful compositions are those which contain 1 part of component (a) and 1 to 100 parts of component (b) by weight and especially 1 part of component (a) and 1 to 10 parts of component (b), for example 1 part of component (a) and 5 parts by weight of component (b).

The compositions of the present invention may be manufactured by any method known to the art. Typically they may be made by grinding together component (a) and component (b) in a mill or grinder where both components are solid.

In many instances we have found it preferable to dissolve the oxy-phosphorus compound which is component (b) in water or an aqueous solvent mixture, and to then add the metal salt or complex which is component (a) and to mill the two components together in the presence of an attrition aid such as pebbles, beads or balls in order to dissolve or disperse the compound which is component (a).

It may also be convenient to mix the metal salt or complex which is component (a) and the free acid of the oxy-phosphorus compound which is component (b) and as a final stage of the preparation of the composition to convert the free acid of the oxy-phosphorus compound into one of its salts.

The compositions of the present invention have antimicrobial properties. We have found that the compositions in accordance with the present invention are active against microbial species such as bacteria, fungi, yeasts and algae, and are suitable for use as industrial biocides.

The compositions of the present invention exhibit good wet state preservation and hence may be used as a cutting fluid preservative and also in cooling water application. The compositions may also be used in paper mill liquors. Furthermore, the compositions may be used to preserve industrially important formulations, especially aqueous based formulations, which are used for coloration, such as dyestuffs and printing inks. The compositions may also be used in the agrochemical industries to preserve formulations such as herbicide and pesticide flowables.

Still further important applications of the compositions of the present invention include their use in hydrocarbon fluids such as diesel fuels. They may also be incorporated into adhesives in order to inhibit microbial spoilage.

The preservation of wood and leather is yet another important application of these compositions.

A particularly preferred use of the compositions of the present invention is the preservation of paints and particularly aqueous based latices, particularly preservation of polyvinylacrylate and especially acrylic latices, particularly those whose pH is above 7, and especially those containing ammonia or amines.

The metal salt or complex which is component (a) of the composition generally exhibits low solubility in water, but often exhibits higher solubility in other polar solvents such as alcohols and ketones. The composition which contains the oxy-phosphorus compound which is component (b), exhibits a higher solubility in water than that of component (a) in the absence of component (b). The composition of the present invention may contain polar solvents other than water which are miscible in water in order to further improve the solubility of component (a) of the composition.

The composition of the present invention may be used alone as an antimicrobial material but may also be used in, or on, a suitable carrier material.

Thus, as a further aspect of the present invention there is provided a biocide composition comprising a carrier and an effective amount of a composition of components (a) and (b) in accordance with the invention.

The carrier is typically a material which shows little, if any, antimicrobial activity and may be, or include, a material which is susceptible to the growth of micro-organisms, particularly bacteria or fungi. The carrier may be a solid, but is preferably a liquid medium and the biocide composition may be a solution, suspension or emulsion of the composition of components (a) and (b) in a liquid carrier. The liquid carrier may be a polar liquid such as acetic acid, N,N-dimethylformamide, propylene glycol, dimethylsulphoxide or N-methyl-2-pyrrolidone in which at least one, and preferably both, of components (a) and (b) are soluble. Alternatively, a mixture of liquids may be used, one being a solvent for at least component (b), such as water, and the other being a non-solvent for both components, and using such a mixture the composition typically comprises an emulsion or droplets of a solution of components (a) and (b) in a solvent therefor dispersed in the non-solvent. If a suspension or emulsion is used, this conveniently contains a surface active agent which is effective to maintain the non-continuous phase as a suspension or emulsion. Any surface active agent known for use in biocide compositions may be used in such a system, for example alkylene oxide adducts of fatty alcohols, alkyl phenol, amines such as ethylene diamine, and anionic surfactants such as those obtained by reacting napththol sulphonates with formaldehyde.

Whereas it is generally preferred in using the composition of the present invention to add component (a) and component (b) simultaneously, for example as a mixture thereof, it will be appreciated that in certain circumstances it may be beneficial to add component (a) and component (b) sequentially.

The amount of the composition comprising component (a) and component (b) which is present in the biocide composition may be just sufficient to have an antimicrobial effect or the composition may be present in a substantially greater proportion. It will be appreciated that the biocide composition may be provided as a concentrated solution which is subsequently diluted for use as an antimicrobial material. The higher concentrations of the biocide composition are useful, for example, in the bulk transportation of the composition. Thus, the amount of the composition of components (a) and (b) which is present in the biocide composition is typically in the range from 0.0001% up to 30% by weight of component (a) of the biocide composition.

The composition of the present invention is especially effective in providing anti-bacterial and/or anti-fungal activity. Thus, the compositions can be used for the treatment of various media to inhibit the growth of micro-organisms.

As a further aspect of the present invention there is provided a method for inhibiting the growth of micro-organisms on, or in, a medium which comprises treating the medium with a composition of components (a) and (b) as hereinbefore defined.

The composition can be used in conditions in which micro-organisms grow and cause problems. Systems in which micro-organisms cause problems include liquid, particularly aqueous, systems such as cooling water liquors, paper mill liquors, metal working fluids, geological drilling lubricants, polymer emulsions, cosmetic formulations such as shampoos and surface coating compositions such as paints, varnishes and lacquers and also solid materials such as wood and leather. The composition of the present invention can be included in such materials to provide an anti-microbial effect. The amount of the composition is typically in the range from 0.0001 up to 10%, preferably 0.0001 up to 5% and especially 0.0005 to 0.1% by weight of component (a) of the composition relative to the system to which it is added. In many cases, microbial inhibition has been obtained with between 0.0005% and 0.01% by weight of component (a) of the composition.

Component (a) of the composition of the present invention may be the only antimicrobial material present or the composition of the present invention may be used together with further compounds having antimicrobial characteristics. The composition may contain more than one compound which is component (a) together with one or more compounds which is component (b). Alternatively, a composition of components (a) and (b) in accordance with the present invention may be used together with one or more known antimicrobial compounds. The use of a mixture of anti-microbial compounds can provide a composition having a broader anti-microbial spectrum and hence one which is more generally effective than the components thereof. The known antimicrobial may be one possessing anti-bacterial, anti-fungal, anti-algal or other antimicrobial characteristic. The mixture of the composition of the present invention with other antimicrobial compounds typically contains from 1 to 99% by weight, relative to the weight of total antimicrobially active compounds, of the composition of components (a) and (b).

As examples of known antimicrobial compounds which may be used, together with the composition of the present invention, there may be mentioned quaternary ammonium compounds such as diethyldodecylbenzyl ammonium chloride; dimethyloctadecyl-(dimethylbenzyl)ammonium chloride; dimethyldidecylammonium chloride; dimethyldidodecylammonium chloride; trimethy-tetradecylammonium chloride; benzyldimethyl($C_{12}$–$C_{18}$ alkyl)ammonium chloride; di-chlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis(beta-hydroxyethyl)ammonium chloride; dodecyl- benzyltrimethylammonium chloride; benzyldimethyl($C_{12}$–$C_{18}$ alkyl) ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; tetrakis(hydroxymethyl)acetylene diurea; 1-(hydroxymethyl)-5,5-dimethylhydantoin and imidazolidinyl urea; amino compounds such as 1,3-bis(2-ethylhexyl)-5-methyl-5aminohexahydropyrimidine; hexamethylene tetra amine; 1,3-bis(4-aminophenoxy)propane; and 2-[(hydroxymethyl)- amino]ethanol; imidazole derivatives such as 1[2-(2,4-dichlorophenyl)-2-(2-propenyloxy)ethyl]-1H-imidazole; 2-(methoxycarbonylamino)-benzimidazole; nitrile compounds such as 2-bromo-2-bromomethylglutaronitrile, 2-chloro-2-chloromethylglutaronitrile, 2,4,5,6-tetrachloroisophthalodinitrile; thiocyanate derivatives such as methylene bis thiocyanate; tin compounds or complexes such as tributyltinoxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiozolin-3-one, 2-methylisothiazolin-3-one, 5-chloro-2-methyl-isothiazolin-3-one, 2-octylisothiazolin-3-one, 4,5-dichloro-2-octyltsothiazolin-3-one, benzisothiazolin-3-one and 2-methylbenzisothiazolin-3-one; thiazole derivatives such as 2-(thiocyanomethylthio)-benzthiazole; and mercaptobenzthiazole; nitro compounds such as tris(hydroxymethyl)nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as gluteraldehyde (pentanedial), p-chlorophenyl-3-iodopropargyl formaldehyde, and glyoxal; amides such as chloracetamide; N,N-bis(hydroxymethyl)chloracetamide; N-hydroxymethylchloracetamide and dithio-2,2-bis(benzmethyl amide); guanidine derivatives such as poly hexamethylene biguanide and 1,6-hexamethylene-bis[5-(4-chlorophenyl)-biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichlorophenoxy)-phenol; thio-bis(4-chlorophenol) and 2-phenylphenol; sulphone derivatives such as diiodomethyl-paratolyl sulphone, 2,3,5,6-tetrachloro-4-(methylsulphonyl) pyridine and hexachlorodimethyl sulphone.

Further aspects of the present invention are described in the following illustrative examples. Unless otherwise stated all refer to parts by weight. Also, the compositions in accordance with the present invention were subjected to evaluation of the antimicrobial properties of the composition. The evaluation was effected, under sterile conditions throughout, in the following manner.

In the microbiological testing, the compositions were tested for anti-microbial activity against bacteria and/or fungi including a yeast. The bacteria used were one or more of *Eshcerichia coli, Pseudomonas aeruginosa, Staphylococcus aureus* and *Bacillus subtills*. The fungi/yeast used were one or more of *Aspergillus niger, Candida albicans, Aureobasidum pullulans, Gliocladium roseum,* and *Penicillium pinophilum.*

These test organisms will be referred to hereafter as EC, PA, SA, BS, AN CA, AP, GR and PP respectively.

Microbiostatic Evaluation

The material to be tested was dissolved in a suitable solvent and the solution obtained diluted with a further quantity of the same solvent to give a desired product concentration.

To a suitable agar medium was added a quantity of the product solution to give a desired concentration of the product. The agar medium containing the product was poured into petri dish plates and allowed to set.

The test organisms were surface inoculated onto the test plates by means of a multi-point inoculator. Each test plate was inoculated with both bacteria, fungi and yeast. The plates were incubated for four days at 25° C.

At the end of the incubation period, the plates were assessed visually for growth of the micro-organisms. The concentration of the product which inhibited the growth of a particular micro-organisms was recorded. This is the minimum inhibitory concentration (M.I.C.).

Generally, the compositions are evaluated against bacteria at the 25 and 100 ppm levels, and against fungi and yeast at the 5, 25 and 100 ppm levels.

EXAMPLE 1

This demonstrates the improved solubility in the presence of pyrophosphate salts of the 1:2 zinc complex obtained from 1-hydroxy-2-pyridinethione.

The 1:2 zinc complex of 1-hydroxy-2-pyridinethione which was prepared according to Example 16 of U.S. Pat. No. 2,809,971 was pebble milled in 0.1 molar solution of various pyrophosphate salts, and the resulting dispersion was gradually diluted with distilled water until a clear solution was obtained. The concentration of the 2:1 zinc complex was then determined.

The results are displayed below.

| Sample | Pyrophosphate salt | Solubility (ppm) |
|---|---|---|
| a | nil | LS 10 |
| b | disodium dihydrogen pyrophosphate | 25–100 |
| c | tetra-sodium pyrophosphate | 250–500 |
| d | tetra lithium pyrophosphate | 100–250 |
| e | dipotassium disodium pyrophosphate | 250–500 |
| f | tetra-ammonium pyrophosphate | 500–1000 |
| g | tetra potassium pyrophosphate | 500–1000 |
| h | disodium bisdiethanolamine pyrophosphate | 250–500 |

LS = less than

EXAMPLE 2

This example demonstrates that the increased solubility of the 1:2 zinc complex obtained from 1-hydroxy-2-pyridinethione in the presence of pyrophosphate salts does not adversely affect the microbiological activity.

1% dispersions of the 1:2 zinc complex obtained from 1-hydroxy-2-pyridinethione were prepared in 0.1 molar solutions of various pyrophosphates as described in Example 1. These dispersions were evaluated by the microbiostatic procedure and the MIC levels determined against a number of bacteria, fungi and a yeast. The MIC values obtained are recorded below in ppm.

| | Fungi/Yeast | | | | | Bacteria | | | |
|---|---|---|---|---|---|---|---|---|---|
| Sample | AN | CA | AP | GR | PP | EC | PA | SA | BS |
| a | 25 | 25 | 5 | 5 | 5 | 25 | NA | 25 | 25 |
| b | 5 | 5 | 5 | 5 | 5 | 25 | NA | 25 | 25 |
| c | 5 | 5 | 5 | 5 | 5 | 25 | NA | 25 | 25 |
| d | 5 | 5 | 5 | 5 | 5 | 25 | NA | 25 | 25 |
| e | 5 | 5 | 5 | 5 | 5 | 25 | NA | 25 | 25 |
| f | 5 | 5 | 5 | 5 | 5 | 25 | NA | 25 | 25 |
| g | 5 | 5 | 5 | 5 | 5 | 25 | 100 | 25 | 25 |
| h | 5 | 5 | 5 | 5 | 5 | 25 | 100 | 25 | 25 |

NA = Not active at 100 ppm

EXAMPLE 3

The 1:2 zinc complex obtained from 3-hydroxy-4-methylthiazol-2(3H)-thione was prepared as described in Example 2 of European Patent No 249328. A finely milled sample exhibited an aqueous solubility of about 5 ppm.

The zinc complex was milled in a 0.1 molar solution of tetrasodium pyrophosphate as described in Example 1. This was then diluted with distilled water until a clear solution was obtained. The solubility of the 1:2 zinc complex obtained from 3-hydroxy-4-methylthiazol-2(3H)-thione was found to be about 10,000 ppm in the presence of the pyrophosphate anion.

EXAMPLE 4

An inoculum was prepared containing Pseudomonas aeruginosa, Proteus rettgeri, Serratia marcescans, Aeromonas hydrophila, Alcaligenes species, Pseudomonas cepacia and Pseudomonas putida by culturing the individual organisms onto nutrient agar and incubating for 24 hours at 30° C. Each of the individual suspensions of the test organisms were then prepared at a concentration of 10E8 cfu/ml in one quarter strength Ringer's solution by means of a Thoma counting chamber. A mixed suspension was obtained by mixing equal volumes of the individual suspensions. This procedure was repeated for each of the three challenges to which the test substrates were subjected, and the concentration of micro-organisms in each substrate after challenge was 2×10E6 cfu/ml.

Aliquots (50 parts) of a standard laboratory acrylic latex and an emulsion paint were prepared containing 0, 10, 25, 50, 100, 125, 250, 500 and 750 ppm of the 1:2 zinc complex of 3-hydroxy-4-methylthiazol-2(3H)thione which was prepared as a 1% dispersion in an aqueous solution of 0.1M tetrasodium pyrophosphate. A 1% dispersion of the 1:2 zinc complex of 1-hydroxy-2-pyridinethiol in an aqueous solution of 0.1M tetrasodiumpyrophosphate was evaluated in the same manner.

The test substrates were then stored at 40° C. for seven days and were then challenged on three separate occasions with 1 part by volume of the mixed suspension of micro-organisms. All the substrates were then incubated at 30° C. and examined for the presence of viable bacteria after 1, 3 and 7 days after each challenge (Phase 1).

Those samples which had achieved sterility were then stored for a further 8 weeks at 30° C., and were then rechallenged and the number of viable organisms again determined (Phase 2).

Viable bacteria were detected by streaking small aliquots onto nutrient agar followed by incubation at 30° C. for 2 days. The presence or absence of colonies was determined visually.

The results are given in Table 1.

TABLE 1

| Biocide/ A.I. conc. ppm | Phase I | | | | | | | | | Phase 2 | | | | | | | | |
|---|---|---|---|---|---|---|---|---|---|---|---|---|---|---|---|---|---|---|
| | Chall 1 | | | Chall 2 | | | Chall 3 | | | Chall 1 | | | Chall 2 | | | Chall 3 | | |
| | 1 | 3 | 7 | 1 | 3 | 7 | 1 | 3 | 7 | 1 | 3 | 7 | 1 | 3 | 7 | 1 | 3 | 7 |
| Acrylic Paint | | | | | | | | | | | | | | | | | | |
| Compound A | | | | | | | | | | | | | | | | | | |
| 10 | 5 | 5 | 0 | 5 | 5 | 5 | 5 | 5 | 5 | N.T. | | | | | | | | |
| 25 | 5 | 3 | 0 | 5 | 4 | 0 | 5 | 5 | 4 | | | | | | | | | |
| 50 | 5 | 3 | 0 | 5 | 4 | 0 | 5 | 4 | 0 | | | | | | | | | |
| 100 | 5 | 2 | 0 | 5 | 4 | 0 | 5 | 4 | 0 | | | | | | | | | |
| 125 | 5 | 2 | 0 | 5 | 4 | 0 | 5 | 4 | 0 | | | | | | | | | |
| 250 | 5 | 1 | 0 | 4 | 4 | 0 | 5 | 4 | 0 | | | | | | | | | |
| 500 | 5 | 1 | 0 | 4 | 3 | 0 | 5 | 3 | 0 | | | | | | | | | |
| 750 | 4 | 1 | 0 | 4 | 3 | 0 | 4 | 4 | 0 | | | | | | | | | |
| Composition B | | | | | | | | | | | | | | | | | | |
| 10 | 5 | 5 | 5 | 5 | 5 | 5 | 5 | 5 | 5 | N.T. | | | | | | | | |
| 25 | 5 | 5 | 5 | 5 | 5 | 5 | 5 | 5 | 5 | | | | | | | | | |
| 50 | 5 | 3 | 0 | 5 | 5 | 5 | 5 | 5 | 5 | | | | | | | | | |
| 100 | 5 | 0 | 0 | 5 | 4 | 0 | 5 | 4 | 0 | | | | | | | | | |
| 125 | 6 | 3 | 0 | 5 | 4 | 0 | 5 | 4 | 0 | | | | | | | | | |
| 250 | 5 | 3 | 0 | 5 | 4 | 0 | 5 | 4 | 0 | | | | | | | | | |
| 500 | 5 | 2 | 0 | 5 | 4 | 0 | 5 | 4 | 0 | | | | | | | | | |
| 750 | 5 | 2 | 0 | 4 | 4 | 0 | 5 | 4 | 0 | | | | | | | | | |

TABLE 1-continued

| Biocide/ | Phase I | | | | | | | | | Phase 2 | | | | | | | | |
|---|---|---|---|---|---|---|---|---|---|---|---|---|---|---|---|---|---|---|
| A.I. | Chall 1 | | | Chall 2 | | | Chall 3 | | | Chall 1 | | | Chall 2 | | | Chall 3 | | |
| conc. ppm | 1 | 3 | 7 | 1 | 3 | 7 | 1 | 3 | 7 | 1 | 3 | 7 | 1 | 3 | 7 | 1 | 3 | 7 |
| Composition C | | | | | | | | | | | | | | | | | | |
| 10 | 5 | 5 | 5 | 5 | 5 | 5 | 5 | 5 | 5 | 5 | 5 | 5 | 5 | 5 | 5 | 5 | 5 | 5 |
| 25 | 5 | 5 | 4 | 5 | 5 | 5 | 5 | 5 | 5 | 5 | 5 | 5 | 5 | 5 | 5 | 5 | 5 | 5 |
| 50 | 5 | 4 | 0 | 5 | 5 | 5 | 5 | 5 | 5 | 5 | 5 | 5 | 5 | 5 | 5 | 5 | 5 | 5 |
| 100 | 5 | 3 | 0 | 5 | 4 | 2 | 4 | 5 | 5 | 5 | 5 | 5 | 5 | 5 | 5 | 5 | 5 | 5 |
| 125 | 5 | 3 | 0 | 5 | 4 | 0 | 5 | 4 | 0 | 5 | 5 | 5 | 5 | 5 | 5 | 5 | 5 | 5 |
| 250 | 5 | 0 | 0 | 5 | 0 | 0 | 5 | 0 | 0 | 5 | 5 | 5 | 5 | 5 | 5 | 5 | 5 | 5 |
| 500 | 2 | 1 | 0 | 2 | 0 | 0 | 5 | 0 | 0 | 5 | 0 | 0 | 5 | 5 | 5 | 5 | 5 | 5 |
| 750 | 0 | 0 | 0 | 0 | 0 | 0 | 5 | 0 | 0 | 5 | 0 | 0 | 4 | 0 | 0 | 3 | 0 | 0 |
| Control (No Biocide) | 5 | 5 | 5 | 5 | 5 | 5 | 5 | 5 | 5 | 5 | 5 | 5 | 5 | 5 | 5 | 5 | 5 | 5 |
| Acrylic Latex | | | | | | | | | | | | | | | | | | |
| Compound A | | | | | | | | | | | | | | | | | | |
| 10 | 5 | 5 | 4 | 5 | 5 | 5 | 5 | 5 | 5 | | | | N.T. | | | | | |
| 25 | 5 | 5 | 4 | 5 | 5 | 3 | 5 | 5 | 5 | | | | | | | | | |
| 50 | 5 | 2 | 2 | 5 | 4 | 0 | 5 | 4 | 0 | | | | | | | | | |
| 100 | 5 | 3 | 0 | 4 | 4 | 0 | 4 | 4 | 0 | | | | | | | | | |
| 125 | 5 | 3 | 0 | 4 | 4 | 0 | 4 | 4 | 0 | | | | | | | | | |
| 250 | 5 | 3 | 0 | 4 | 4 | 0 | 4 | 4 | 0 | | | | | | | | | |
| 500 | 5 | 3 | 0 | 4 | 4 | 0 | 3 | 2 | 0 | | | | | | | | | |
| 750 | 4 | 2 | 0 | 3 | 3 | 0 | 2 | 0 | 0 | | | | | | | | | |
| Composition B | | | | | | | | | | | | | | | | | | |
| 10 | 5 | 5 | 5 | 5 | 5 | 5 | 5 | 5 | 5 | | | | N.T. | | | | | |
| 25 | 5 | 5 | 3 | 5 | 5 | 5 | 5 | 5 | 5 | | | | | | | | | |
| 50 | 5 | 4 | 3 | 5 | 5 | 5 | 5 | 5 | 5 | | | | | | | | | |
| 100 | 5 | 4 | 4 | 5 | 5 | 5 | 5 | 5 | 5 | | | | | | | | | |
| 125 | 5 | 5 | 3 | 5 | 5 | 5 | 5 | 5 | 5 | | | | | | | | | |
| 250 | 5 | 4 | 4 | 5 | 5 | 5 | 5 | 5 | 5 | | | | | | | | | |
| 500 | 5 | 4 | 2 | 5 | 5 | 2 | 5 | 5 | 2 | | | | | | | | | |
| 750 | 5 | 4 | 2 | 5 | 5 | 1 | 5 | 5 | 2 | | | | | | | | | |
| Composition C | | | | | | | | | | | | | | | | | | |
| 10 | 5 | 5 | 5 | 5 | 5 | 5 | 5 | 5 | 5 | 5 | 5 | 5 | 5 | 5 | 5 | 5 | 5 | 5 |
| 25 | 5 | 4 | 5 | 5 | 5 | 5 | 5 | 5 | 5 | 5 | 5 | 5 | 5 | 5 | 5 | 5 | 5 | 5 |
| 50 | 5 | 4 | 4 | 5 | 5 | 5 | 5 | 5 | 0 | 5 | 5 | 5 | 5 | 5 | 5 | 5 | 5 | 5 |
| 100 | 5 | 0 | 0 | 4 | 0 | 0 | 5 | 4 | 3 | 5 | 5 | 5 | 5 | 5 | 5 | 5 | 5 | 5 |
| 125 | 4 | 0 | 0 | 4 | 1 | 0 | 5 | 3 | 0 | 5 | 3 | 5 | 5 | 5 | 5 | 5 | 5 | 5 |
| 250 | 3 | 0 | 1 | 3 | 0 | 0 | 5 | 0 | 0 | 5 | 2 | 0 | 4 | 4 | 0 | 3 | 3 | 0 |
| 500 | 2 | 0 | 0 | 3 | 0 | 0 | 4 | 0 | 0 | 2 | 0 | 0 | 4 | 2 | 0 | 0 | 0 | 0 |
| 750 | 0 | 0 | 0 | 2 | 0 | 0 | 4 | 0 | 0 | 2 | 0 | 0 | 4 | 0 | 0 | 0 | 0 | 0 |
| Control (No Biocide) | 5 | 5 | 5 | 5 | 5 | 5 | 5 | 5 | 5 | 5 | 5 | 5 | 5 | 5 | 5 | 5 | 5 | 5 |

Key
5 = Confluent growth
4 = Heavy growth
3 = Moderate growth
2 = Slight growth
1 = Trace growth
0 = No growth
NT = Not tested Compound A is the 1:2 zinc complex of 3-hydroxy-4-methylthiazol-2(3H)thione prepared as described in Example 2 of EP 249328

Composition B is a 1% dispersion of compound A in an aqueous solution of 0.1M tetrasodium pyrophosphate.

Composition C is the 1:2 zinc complex of 1-hydroxy-2-pyridinethione prepared as described in Example 16 of U.S. Pat. No. 2,809,971 and evaluated as a 1% dispersion in an aqueous solution of 0.1M tetrasodium pyrophosphate.

EXAMPLE 5

The procedure described in Example 4 was repeated using a 1% aqueous dispersion of the 1:2 zinc complex obtained from 1-hydroxy-2-pyridinethione in an aqueous solution of 0.1M tetrasodium pyrophosphate, and a sample of the zinc complex of pyridinethione which is commercially available as Zinc Omadine from Olin Chemicals.

In this example the biocides were also evaluated at the higher concentrations of 1500 and 1920 ppm.

The results are displayed in Table 2, which shows the end concentration of the biocide at which control was achieved.

TABLE 2

| | Acrylic Paint | | Acrylic Latex | |
|---|---|---|---|---|
| Biocide | Phase 1 | Phase 2 | Phase 1 | Phase 2 |
| ZPT/Na pyrophosphate (a) | 100–125 | 500–750 | 50–125 | 125–250 |
| ZPT (b) | 120 | GT 1920 | NT | NT |

Key
GT = Greater than
NT = Not tested
a = a solution containing 1% 1:2 zinc complex of 1-hydroxy-2-pyridinethione
b = a dispersion of 1:2 zinc complex of 1-hydroxy-2-pyridinethione commercially available as Zinc Omadine from Olin Chemicals.

EXAMPLE 6

Aliquots (10 parts by volume) of a Difco algal broth medium were prepared containing 0.16, 0.64, 2.5 and 10 ppm of the 1:2 zinc complex of 1-hydroxy-2-pyridinethione which was prepared as a 1% aqueous dispersion in 0.1M pyrophosphate solution as described in Example 1. A sample containing no biocide was include as a control.

The above aliquots were then inoculated with 0.1 parts by volume of a mixed algal suspension of 7 day cultures of the following algae.

*Stichococcus bacillaris*
*Gloecapsa alpicola*
*Nostoc commune*
*Trentepohlia aurea*

The samples were then incubated at 15° to 20° C. and exposed to artificial illumination of between 700 and 1200 LUX over a two week period, where the illumination was provided from the side and the light varied over a 24 hour period to give 16 hours illumination and 8 hours darkness.

After a two week incubation period, the samples were re-challenged with the mixed algal inoculum, and again examined after a 4 week incubation period. The minimum inhibitory concentration at which algal growth was suppressed was then established by visual assessment.

The results are tabulated in Table 3.

TABLE 3

| Sample | Pyrophosphate Salt | MIC (ppm) |
|---|---|---|
| a | nil | 0.64 |
| b | disodium dihydrogen pyrophosphate | 0.64 |
| c | tetra sodium pyrophosphate | 2.5 |
| d | tetra lithium pyrophosphate | 0.64 |
| e | dipotassium disodium pyrophosphate | 0.16 |
| f | tetra ammonium pyrophosphate | 0.64 |
| g | tetra potassium pyrophosphate | 0.64 |
| h | disodium bisdiethanolamine pyrophosphate | 0.64 |

EXAMPLE 7

A shampoo having the following composition
Empicol* E8B70 16.5 parts
Empilan* 2502 2.0 parts
Empigen* BB 5.0 parts
Sodium chloride 1.0 part
Citric Acid to pH7
Water to 100 parts

*Empicol, Empilan and Empigen are registered Trademarks of Albright and Wilson, was prepared by stirring the Empicol ESB70 in water, and then adding the Empilan 2502 followed by the Empigen BB to give a clear homogenous solution. An aqueous solution of citric acid was added with stirring to give a pH of 7. Finally, the sodium chloride was added and the whole diluted to parts by adding water.

Aliquots (20 parts) of the above shampoo were then prepared with concentrations of the biocides indicated in Table 4 at 500, 125, 31.25 and 7.8 ppm of active ingredient.

The above samples were then challenged with a 0.2 parts by volume inoculum of a 24 hour culture of Pseudomonas aeruginosa (ATCC 19429) containing approximately $1 \times 10^8$ colony forming units (cfu's) per milliliter. The samples were then incubated in the dark at 25° C., 1 milliliter samples taken after 24 hours, 48 hours and 7 days and the number of surviving bacteria determined.

The results are shown in Table 4.

TABLE 4

| SAMPLE | CONC (PPM) | VIABLE BACTERIA AFTER | | |
|---|---|---|---|---|
| | | 24 HRS | 48 HRS | 7 DAYS |
| ZDM | 500 | LT 10 | LT 10 | LT 10 |
| | 125 | LT 10 | LT 10 | GT 3 × E4 |
| | 31.25 | 5.5 × E3 | GT 3 × E4 | GT 3 × E4 |
| | 7.8 | GT 3 × E4 | GT 3 × E4 | GT 3 × E4 |
| ZDMP | 500 | LT 10 | LT 10 | LT 10 |
| | 125 | 1 × E2 | GT 3 × E4 | GT 3 × E4 |
| | 31.25 | 1.6 × E2 | GT 3 × E4 | GT 3 × E4 |

TABLE 4-continued

| SAMPLE | CONC (PPM) | VIABLE BACTERIA AFTER | | |
|---|---|---|---|---|
| | | 24 HRS | 48 HRS | 7 DAYS |
| | 7.8 | 3.3 × E2 | GT 3 × E4 | GT 3 × E4 |
| EBD | 500 | GT 3 × E4 | GT 3 × E4 | GT 3 × E4 |
| | 125 | GT 3 × E4 | GT 3 × E4 | GT 3 × E4 |
| | 31.25 | GT 3 × E4 | GT 3 × E4 | GT 3 × E4 |
| | 7.8 | GT 3 × E4 | GT 3 × E4 | GT 3 × E4 |
| EBDP | 500 | LT 10 | LT 10 | LT 10 |
| | 125 | LT 10 | LT 10 | LT 10 |
| | 31.25 | LT 10 | LT 10 | LT 10 |
| | 7.8 | LT 10 | LT 10 | LT 10 |
| Control | | 2 × E2 | 3.6 × E7 | 4.7 × E8 |

LT = less than
GT = greater than
E = logarithmic power of 10
ZDM is the zinc complex of dimethyldithiocarbamate added as an aqueous dispersion.
ZDMP is a 1% dispersion of the zinc complex of dimethyldithiocarbamate in an aqueous solution of 0.1 M tetrapotassium pyrophosphate
EBD is the zinc complex of ethylene bis dithiocarbamate added as an aqueous dispersion
EBDP is a 1% dispersion of the zinc complex of ethylene bisdithiocarbamate in an aqueous solution of 0.1 M tetrapotassium pyrophosphate.
Empicol ESB70 is a 60% aqueous solution of sodium laurylethoxysulphate
Empilan 2502 is coconut diethanolamide
Empigen BB is an aqueous 30% solution of an alkyl ($C_{12}/C_{14}$) betaine.

EXAMPLE 8

This example demonstrates the increased solubility of the zinc complex of dimethyldithiocarbamate and the zinc complex of ethylenebisdithiocarbamate in the presence of 0.1M tetrasodium pyrophosphate solution. These solutions were prepared by the method described in Example 1.

| Sample | | Pyrophosphate Salt (0.1 M) | Solubility (ppm) |
|---|---|---|---|
| a | ZDM | nil | LS 5 |
| b | ZDM | tetrasodium pyrophosphate | 10–100 |
| c | EBD | nil | LS 5 |
| d | EBD | tetrasodium pyrophosphate | 10–100 |

LS = less than
ZDM = is the zinc complex of dimethyldithiocarbamate
EBD = is the zinc complex of ethylenebisdithiocarbamate.

EXAMPLE 9

The procedure described in Example 7 was repeated, except that the compounds and formulations used in that example were replaced by a commercially available formulation of zinc pyrithione or a 1% dispersion of the 2:1 complex of 1-hydroxy-2-pyridinethione and zinc in an aqueous solution of 0.1M tetrasodium pyrophosphate prepared as described in Example 1. The results are detailed in Table 5.

TABLE 5

| SAMPLE | CONC (PPM) | VIABLE BACTERIA AFTER | | |
|---|---|---|---|---|
| | | 24 HRS | 48 HRS | 7 DAYS |
| ZPT | 500 | LT 10 | LT 10 | LT 10 |
| | 125 | LT 10 | LT 10 | LT 10 |
| | 31.25 | LT 10 | 2.8 × E5 | GT 3 × E6 |
| | 7.8 | GT 3 × E6 | GT 3 × E6 | GT 3 × E6 |
| ZPT/Pyr | 500 | LT 10 | LT 10 | LT 10 |
| | 125 | LT 10 | LT 10 | LT 10 |
| | 31.25 | LT 10 | LT 10 | LT 10 |

TABLE 5-continued

| | CONC | VIABLE BACTERIA AFTER | | |
|---|---|---|---|---|
| SAMPLE | (PPM) | 24 HRS | 48 HRS | 7 DAYS |
| | 7.8 | GT 3 × E6 | GT 3 × E6 | GT 3 × E6 |

LT = less than
GT = greater than
E = logarithmic power of 10
ZPT is an aqueous 1% by weight dispersion of the 1:2 zinc complex of 1-hydroxy-2-pyridinethione.
ZPT/Pyr is a 1% dispersion of the 1:2 zinc complex of 1-hydroxypyridinethione in an aqueous solution of 0.1 M tetra sodium pyrophosphate.

We claim:

1. A biocidal composition comprising:
   (a) a metal salt or complex of an organic compound of general formula III

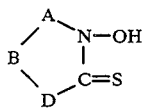

III wherein
   A is a group —C(R$^2$)$_2$—, —CR$^2$= or —CH=CH—;
   B is —C(R$^2$)$_2$— or —CR$^2$=;
   D is —C(R$^2$)$_2$—, —CR$^2$= or sulphur;
   R$^2$ is hydrogen, C$_{1-5}$-alkyl or phenyl; and
   (b) an oxy-phosphorus acid or alkali metal or ammonium salt thereof, said component (b) present in an amount sufficient to improve the aqueous solubility of component (a).

2. A composition as claimed in claim 1 in which the metal salt or complex of the organic compound is a metal salt or complex of a metal of groups IIIA to VA or IB to VIIB of the periodic table.

3. A composition as claimed in claim 2 in which the metal is copper, zinc or iron.

4. A composition as claimed in claim in which the metal salt or complex with the organic compound of general formula III is the 2:1 complex of 3-hydroxy-4-methylthiazol-2(3H)-thione and zinc; 4,5-dimethyl-3-hydroxythiazol-2(3H)-thione and copper; 4,5-dimethyl-3-hydroxythiazol-2(3H)-thione and zinc; 4-ethyl-3-hydroxy-5-methylthiazol-2(3H)-thione and zinc, or 1-hydroxy-2-pyridinethione and zinc.

5. A composition as claimed in claim 1 where the acid or salt is selected from orthophosphates, orthophosphites, hypophosphites, triphosphates, hexametaphosphates or pyrophosphates.

6. A composition as claimed in claim 1 which comprises the 1:2 zinc complex of 1-hydroxy-2-pyridinethione and tetrasodium pyrophosphate or the 1:2 zinc complex of 3-hydroxy-4-methylthiazol-2(3H)thione and tetrasodium pyrophosphate.

7. A composition as claimed in claim 1 which comprises the 1:2 zinc complex of 1-hydroxy-2-pyridinethione and tetrapotassium pyrophosphate or the 1:2 zinc complex of 3-hydroxy-4-methylthiazol-2(3H)thione and tetrapotassium pyrophosphate.

8. A composition as claimed in claim 1 in which the ratio of component a) to component b) is between 1:1 and 1:10,000 parts by weight.

9. A composition as claimed in claim 1 wherein R$^2$ is hydrogen, methyl or ethyl.

10. A medium which is susceptible to microbial attack which contains a composition as claimed in claim 1 in a sufficient amount to inhibit micro-organisms.

11. A medium as claimed in claim 10 which is selected from a cooling water system, a paper mill liquor, a metal working fluid, a geological drilling lubricant, a polymer emulsion, a cosmetic formulation, a paint, a lacquer, a varnish, a hydrocarbon fluid, an adhesive, a dyestuff or ink formulation, an agrochemical formulation, leather or wood.

* * * * *